(12) United States Patent
He et al.

(10) Patent No.: US 11,982,658 B2
(45) Date of Patent: May 14, 2024

(54) METHODS, APPARATUSES, AND SYSTEMS FOR CALIBRATING GAS DETECTING APPARATUSES

(71) Applicant: Honeywell International Inc., Charlotte, NC (US)

(72) Inventors: Xiangcai He, Charlotte, NC (US); Chuang Huang, Charlotte, NC (US); Li Liu, Charlotte, NC (US); Yong Wang, Charlotte, NC (US)

(73) Assignee: Honeywell International Inc., Charlotte, NC (US)

( * ) Notice: Subject to any disclaimer, the term of this patent is extended or adjusted under 35 U.S.C. 154(b) by 50 days.

(21) Appl. No.: 17/804,951

(22) Filed: Jun. 1, 2022

(65) Prior Publication Data
US 2022/0404324 A1 Dec. 22, 2022

(30) Foreign Application Priority Data
Jun. 16, 2021 (CN) .......................... 202110666485.8

(51) Int. Cl.
*G01N 33/00* (2006.01)
*G01M 3/38* (2006.01)

(52) U.S. Cl.
CPC .......... *G01N 33/0006* (2013.01); *G01M 3/38* (2013.01)

(58) Field of Classification Search
CPC .......... G01N 33/0006; G01N 27/4175; G01N 33/007; G01N 27/4163; G01N 21/3504;
(Continued)

(56) References Cited

U.S. PATENT DOCUMENTS 4,279,618 A * 7/1981 Barden .............. G01N 33/0006
436/171
5,648,601 A * 7/1997 Katoh .................. G01N 33/007
73/1.06
(Continued)

FOREIGN PATENT DOCUMENTS

CN 110850040 2/2020
CN 212132051 U * 12/2020 ............... F17D 1/02
(Continued)

OTHER PUBLICATIONS

EPO The Hauge, Extended European Search Report for EP Application No. 22177105.8 dated Oct. 18, 2022 (9 pages).
(Continued)

*Primary Examiner* — Herbert K Roberts
*Assistant Examiner* — Anthony W Megna Fuentes
(74) *Attorney, Agent, or Firm* — Alston & Bird LLP

(57) ABSTRACT

Methods, apparatuses and systems for calibrating gas detectors are disclosed. An example calibration apparatus may have a gas supply element configured to provide a background gaseous substance within at least a portion of the calibration apparatus, a nebulizing element configured to generate the testing gaseous substance by transforming a testing solution in conjunction with the background gaseous substance, a pressure control element configured to regulate airflow in order to maintain a constant air pressure within the at least a portion of the calibration apparatus, and a controller component in electronic communication with the gas supply element, the nebulizing element and the pressure control element.

18 Claims, 6 Drawing Sheets

(58) Field of Classification Search
CPC .......... G01N 21/274; G01N 35/00693; G01N 2001/2893; G01N 3/38; Y10T 436/25; Y10T 436/10
See application file for complete search history.

(56) References Cited

U.S. PATENT DOCUMENTS

| | | |
|---|---|---|
| 9,675,922 B2 | 6/2017 | Ryan et al. |
| 2006/0196518 A1 | 9/2006 | Hon |
| 2008/159917 A1 | 7/2008 | Tobias |
| 2012/0097556 A1* | 4/2012 | Gascoine ............ B65D 1/0223 206/216 |
| 2014/0001280 A1 | 1/2014 | Field et al. |

FOREIGN PATENT DOCUMENTS

| | | | |
|---|---|---|---|
| JP | 2013057641 A * | 3/2013 | ............ G01N 30/06 |
| WO | 2001/009600 | 2/2001 | |
| WO | 2001/025781 | 4/2001 | |
| WO | 2005/052571 | 6/2005 | |
| WO | 2014/209899 | 12/2014 | |
| WO | WO-2020214550 A1 * | 10/2020 | ............ G01N 27/66 |

OTHER PUBLICATIONS

Taylor, Howard E., Inorganic Substances, Mass Spectrometric in the Analysis of . . . Published 2006 in the Encyclopedia of Analytical Chemistry (13 pages).

* cited by examiner

METHODS, APPARATUSES, AND SYSTEMS FOR CALIBRATING GAS DETECTING APPARATUSES

CROSS-REFERENCE TO RELATED APPLICATIONS

This application claims priority pursuant to 35 U.S.C. 119(a) to China Patent Application No. 202110666485.8, filed Jun. 16, 2021, which application is incorporated herein by reference in its entirety.

BACKGROUND

Gas detecting apparatuses may detect and/or measure the concentration level of gaseous substance and/or compounds in a gaseous substance, including, for example, organic compounds and inorganic compounds. Many gas detecting apparatuses are plagued by technical challenges and limitations. For example, gas detecting apparatuses may require calibration prior to use in order to produce accurate readings. In many examples, such calibration techniques may be time consuming and/or technically complex.

BRIEF SUMMARY

Various embodiments described herein relate to methods, apparatuses, and systems for calibrating gas detecting components, devices and apparatuses (e.g., a gas detector).

In accordance with various examples of the present disclosure, a apparatus is provided. The apparatus may comprise a gas supply element configured to provide a background gaseous substance within at least a portion of the calibration apparatus, a nebulizing element configured to generate the testing gaseous substance by transforming a testing solution in conjunction with the background gaseous substance, a pressure control element configured to regulate airflow in order to maintain a constant air pressure within the at least a portion of the calibration apparatus, and a controller component in electronic communication with the gas supply element, the nebulizing element and the pressure control element.

In accordance with various examples of the present disclosure, a method is provided. The method may comprise, providing, by a gas supply element, a background gaseous substance within at least a portion of a calibration apparatus, transforming, by a nebulizing element and in conjunction with the background gaseous substance, a testing solution disposed within the at least a portion of the calibration apparatus into a testing gaseous substance; and regulating, by a pressure control element, airflow in order to maintain a constant air pressure within the at least a portion of the calibration apparatus.

The foregoing illustrative summary, as well as other exemplary objectives and/or advantages of the disclosure, and the manner in which the same are accomplished, are further explained in the following detailed description and its accompanying drawings.

BRIEF DESCRIPTION OF THE DRAWINGS

The description of the illustrative embodiments may be read in conjunction with the accompanying figures. It will be appreciated that, for simplicity and clarity of illustration, elements illustrated in the figures have not necessarily been drawn to scale, unless described otherwise. For example, the dimensions of some of the elements may be exaggerated relative to other elements, unless described otherwise. Embodiments incorporating teachings of the present disclosure are shown and described with respect to the figures presented herein, in which.

DETAILED DESCRIPTION OF THE INVENTION

Figure 1:
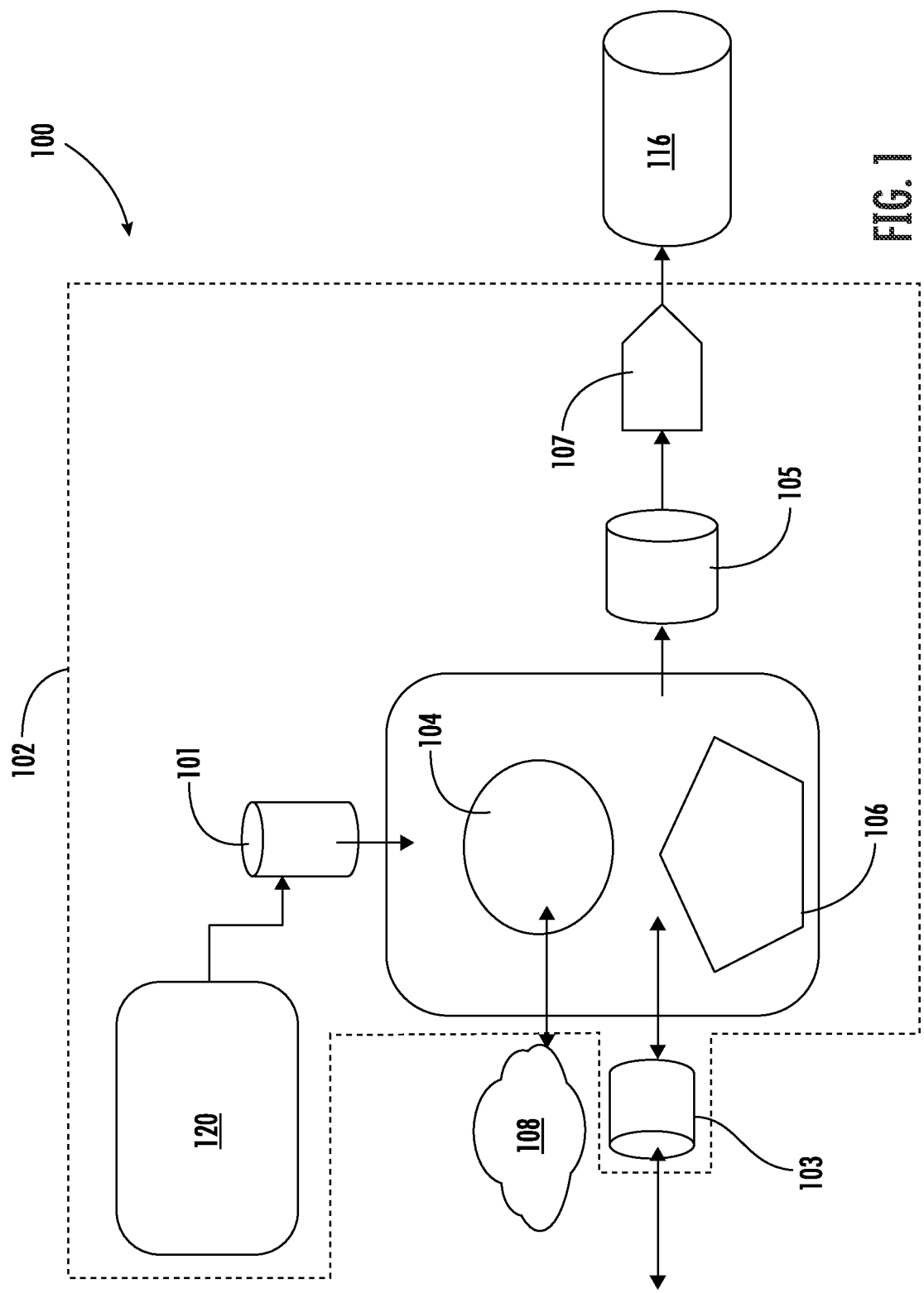
FIG. 1 illustrates an example schematic diagram depicting a system in accordance with various embodiments of the present disclosure.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout.

The components illustrated in the figures represent components that may or may not be present in various embodiments of the present disclosure described herein such that embodiments may include fewer or more components than those shown in the figures while not departing from the scope of the present disclosure. Some components may be omitted from one or more figures or shown in dashed line(s) for visibility of the underlying components.

The phrases "in an example embodiment," "some embodiments," "various embodiments," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "example" or "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that a specific component or feature is not required to be included or to have the characteristic. Such components or features may be optionally included in some embodiments, or may be excluded.

The term "electronically coupled" or "in electronic communication with" in the present disclosure refer to two or more electrical elements (for example, but not limited to, an example processing circuitry, communication module, input/output module memory, gas detecting apparatus) and/or electric circuit(s) being connected through wired means (for example but not limited to, conductive wires or traces) and/or wireless means (for example but not limited to, wireless network, electromagnetic field), such that data and/or information (for example, electronic indications, signals) may be transmitted to and/or received from the electrical elements and/or electric circuit(s) that are electronically coupled.

Various apparatuses (such as, but not limited to, a gas detector) may measure the concentration level of volatile organic compounds in a gaseous substance. The term "volatile organic compound" (or "VOC") may refer to organic compounds that may have a high vapor pressure at ordinary room temperature (i.e., they may easily become gases or vapors). Example chemicals in example VOCs may include, for example, but not limited to, formaldehyde, methane, and benzene. A high-level concentration of VOCs in a gaseous substance (for example, indoor air or outdoor air) may cause adverse effect on health and environment. As such, gas detectors may be utilized to measure and monitor the concentration level of VOCs in various indoor and/or outdoor locations.

As noted above, gas detecting apparatuses may require calibration prior to use in order to produce accurate readings. For example, a gas detecting apparatus may need to be calibrated in order to accurately detect a concentration level of a particular VOC. In some examples, a liquid solution containing a VOC may be provided and a grinding method/technique applied to transform the liquid solution into a gaseous substance for calibration of a gas detecting apparatus prior to use (e.g., prior to deployment in the field or delivery to a customer). Such techniques for calibrating a gas detecting apparatus pose many technical challenges and limitations.

In various examples, a VOC or compound may be provided in a liquid solution for testing due to regulations and safety considerations. By way of example, in order to produce a gaseous substance containing a VOC for calibration purposes, a grinding method may be employed in which a liquid solution containing the VOC may be mixed with other agents within a closed-loop tubing system until the VOC is fully evaporated (i.e., transformed or converted into a gaseous substance). In some examples, it may take an hour or longer for a VOC or compound to be fully evaporated using such techniques. As such, the grinding method and similar techniques may be time consuming and complex and, in some cases, may fail to transform an example liquid solution containing a VOC into a stable gaseous substance. In some cases, heating of the testing solution during the grinding method may result in calibration errors (e.g., VOC decomposition) which may in turn cause the calibrated gas detecting apparatus to produce inaccurate readings. Further, when utilizing the grinding method, negative pressure may be generated which may also lead to the calibrated gas detecting apparatus being improperly calibrated and result in inaccurate readings.

In accordance with various embodiments of the present disclosure, example methods, apparatuses and systems are provided.

For example, the present disclosure may provide a calibration apparatus configured to generate a testing gaseous substance. The calibration apparatus may comprise a gas supply element configured to provide a background gaseous substance within at least a portion of the calibration apparatus, a nebulizing element configured to generate the testing gaseous substance by transforming a testing solution in conjunction with the background gaseous substance, a pressure control element configured to regulate airflow in order to maintain a constant air pressure within the at least a portion of the calibration apparatus, and a controller component in electronic communication with the gas supply element, the nebulizing element and the pressure control element. In some examples, the calibration apparatus further comprises a sealable window disposed adjacent the nebulizing element, wherein the sealable window is configured to receive the testing solution. In some examples, the calibration apparatus further comprises a gas flow channel comprising at least one gas inlet and at least one gas outlet through which a gaseous substance may enter or exit the calibration apparatus. In some examples, the calibration apparatus further comprises at least one valve connected to the gas flow channel configured to regulate a flow of the gaseous substance. In some examples, the at least one valve is disposed between the calibration apparatus and a gas detecting apparatus. In some examples, the controller component is further configured to, in response to determining that the testing gaseous substance satisfies one or more target parameters, transmit a control indication to actuate the at least one valve in order to cause at least a portion of the testing gaseous substance to enter the gas detecting apparatus. In some examples, the pressure control element comprises a pressure sensor. In some examples, the pressure control element comprises a gas bag. In some examples, the controller component is further configured to, in response to determining that the testing solution is fully transformed, cause the at least a portion of the testing gaseous substance to enter a gas detecting apparatus in conjunction with output air of a pump. In some examples, the nebulizing element comprises an ultrasonic nebulizer. In some examples, the gas detecting apparatus comprises a photoionization detector or an infrared leak detector.

In accordance with some embodiments of the present disclosure, a method is provided. The method may comprise providing, by a gas supply element, a background gaseous substance within at least a portion of a calibration apparatus, transforming, by a nebulizing element and in conjunction with the background gaseous substance, a testing solution disposed within the at least a portion of the calibration apparatus into a testing gaseous substance, and regulating, by a pressure control element, airflow in order to maintain a constant air pressure within the at least a portion of the calibration apparatus. In some examples, the method may comprise depositing, via a sealable window disposed adjacent the nebulizing element, the testing solution. In some examples, the calibration apparatus comprises a gas flow channel comprising at least one gas inlet and at least one gas outlet through which a gaseous substance may enter or exit the calibration apparatus. In some examples, the calibration apparatus comprises at least one valve connected to the gas flow channel configured to regulate a flow of the gaseous substance. In some examples, the method comprises, in response to determining, by a controller component in electronic communication with the nebulizing element and the pressure control element, that the testing gaseous substance satisfies one or more parameters, transmitting, by the controller component, a control indication to actuate the at least one valve. In some examples, the pressure control element comprises a pressure sensor. In some examples, the pressure control element comprises a gas bag. In some examples, the method further comprises, in response to determining, by the controller component, that the testing solution is fully transformed, actuating, by the controller component, a pump in order to cause at least a portion of the testing gaseous substance to enter a gas detecting apparatus in conjunction with output air of the pump. In some examples, the nebulizing element comprises an ultrasonic nebulizer. In some examples, the gas detecting apparatus comprises a photoionization detector or an infrared leak detector.

Referring now to FIG. 1, an example schematic diagram depicting an example system 100 in accordance with various embodiments of the present disclosure in provided. As depicted, the system 100 comprises a calibration apparatus 102 and a gas detecting apparatus 116. The calibration apparatus 102 may be configured to provide a testing gaseous substance in order to calibrate the gas detecting apparatus 116. The example gas detecting apparatus 116 may be or comprise, for example, without limitation, a photoionization detector (PID), an infrared leak detector, electrochemical sensor detector, calibration dock station or the like.

As depicted in FIG. 1, the example system 100 comprises a calibration apparatus 102. The calibration apparatus 102 may be configured to receive a testing solution (e.g., a compound, VOC or the like dispersed in a liquid). The calibration apparatus 102 may be configured to transform the testing solution into a testing gaseous substance in order to calibrate a gas detecting apparatus 116. As depicted in FIG. 1, the calibration apparatus 102 comprises a gas supply element 120, a pressure control element 104, a nebulizing element 106, a first valve 101, a second valve 103, a third valve 105 and a pump 107.

The example calibration apparatus 102 may define a gas flow channel. The gas flow channel may refer to one or more passageways having at least one gas inlet and at least one gas outlet through which a background gaseous substance and a testing solution may enter (e.g., from the gas supply element 120), flow through and be expelled from the calibration apparatus 102. The gas flow channel may be or comprise, for example, without limitation, pipes, conduits, tubular structures, and/or the like. In various examples, the gas flow channel(s) may comprise valves which operate to control and/or regulate the flow of a gaseous substance through the calibration apparatus 102. The example valves may be bi-directional valves configured to permit a gaseous substance to flow in both directions with respect to a location within the gas flow channel. In some examples, the valves may be or comprise solenoid valves, pneumatic valves, or the like.

Referring again to FIG. 1, the calibration apparatus 102 may comprise a gas supply element 120 configured to supply a background gaseous substance and a nebulizing element 106 configured to receive a testing solution (e.g., comprising a VOC). In various examples, the gas supply element 120 and the calibration apparatus 102 may form a unitary body or, in some cases, may be distinct from one another. The gas supply element 120 may be or comprise a metallic gas cylinder or any other suitable device for housing/securing a gaseous substance. In some examples, the gaseous substance may be or comprise a background gaseous substance such as Nitrogen ($N_2$). The nebulizing element 106 may comprise a window, cavity, or the like for depositing/mixing the testing solution into the background gaseous substance such that the background gaseous substance and the testing solution can be conveyed to the calibration apparatus 102. Subsequent to depositing the testing solution, the window or cavity may be closed or sealed prior to proceeding with further operations. In some examples, the testing solution may be deposited into another component or from another portion of the calibration apparatus 102.

The background gaseous substance and testing solution may enter the calibration apparatus 102 through one or more openings (e.g., gas inlet(s)/outlet(s)) on a surface of the housing of the calibration apparatus 102 and may then be conveyed through the calibration apparatus 102. By way of example, as depicted in FIG. 1, the background gaseous substance may be conveyed via a gas flow channel from a gas inlet disposed adjacent the first valve 101 of the calibration apparatus 102. The first valve 101 may be configured to actuate (e.g., open automatically) in response to receiving a control signal from a controller component to commence calibration operations. As noted above, the testing solution may be deposited directly into the nebulizing element 106, for example, via a sealable window or aperture.

As noted above, and as depicted in FIG. 1, the calibration apparatus 102 comprises a pressure control element 104. The pressure control element 104 may be configured to regulate/control air pressure within at least a portion of the calibration apparatus 102. The pressure control element 104 may be a gas bag (e.g., comprising textile, paper or the like). As the background gaseous substance/testing solution flow into the gas flow channel of the calibration apparatus 102, the air pressure within the housing of the calibration apparatus 102 may increase. In response, air 108 disposed within the pressure control element 104 may be expelled from the pressure control element 104/calibration apparatus 102 (e.g., through a gas inlet/outlet) in order to maintain a steady system air pressure within at least a portion of the housing of the calibration apparatus 102. In some examples, when the air 108 has been expelled/removed from the pressure control element 104 and the calibration apparatus 102 contains a target amount of the background gaseous substance supplied by the gas supply element 120, one or more valves may be deactivated by providing a control signal to deactivate or close the valve(s). For example, the first valve 101 and/or the second valve 103 may be deactivated concurrently by providing a control signal to deactivate or close the first valve 101 and/or the second valve 103. Accordingly a target amount of a background gaseous substance/testing solution having a uniform concentration required for accurate calibration can be provided.

As noted above, and as depicted in FIG. 1, the calibration apparatus 102 comprises a nebulizing element 106. In various examples, the nebulizing element 106 may be configured to transform (e.g., condition, nebulize, aerosolize, vaporize, disperse, and/or the like) a testing solution (e.g., comprising a VOC) in conjunction with a background gaseous substance in order to provide a testing gaseous substance with a uniform concentration of the target substance or compound (e.g., VOC) dispersed therein. In some examples, the nebulizing element 106 may be or comprise an ultrasonic nebulizer. The example ultrasonic nebulizer may operate to transform the testing solution and the background gaseous substance into the testing gaseous substance without using heat which may degrade the testing solution leading to inaccurate calibration operations. For example, if a target compound is not uniformly dispersed within the target gaseous substance, an example gas detecting apparatus may generate inaccurate measurements during calibration which may result in malfunction and suboptimal performance of the gas detecting apparatus when deployed in the field.

The example ultrasonic nebulizer may comprise transducers which produce ultrasonic sound waves capable of converting a testing solution into small droplets when the sound waves are incident on the testing solution. In various examples, the nebulizing element 106 may be or comprise other types of components/devices capable of transforming (e.g., conditioning, nebulizing, aerosolizing, vaporizing, dispersing, and/or the like) a liquid solution into a resultant testing gaseous substance such as a humidifier, jet nebulizer or mesh nebulizer. Additionally, the nebulizing element 106 is capable of transforming a testing solution (e.g., comprising a VOC) into a testing gaseous substance within a short period of time. In some examples, within 10 seconds or less.

As noted above, and as further depicted in FIG. 1, the system 100 comprises a gas detecting apparatus 116 operatively coupled and/or connected to the calibration apparatus 102. In various examples, the gas detecting apparatus 116 may be calibrated when operated in conjunction with the calibration apparatus 102. For instance, during calibration operations, a number of measurements may be taken in relation to the testing gaseous substance in order to ensure that the gas detecting apparatus 116 satisfies one or more target operational parameters. By way of example, a concentration of a particular VOC dispersed within the testing gaseous substance may be measured in order to ensure that the gas detecting apparatus 116 is configured to accurately detect the VOC.

As depicted in FIG. 1, the calibration apparatus 102 comprises a pump 107. The pump 107 may be configured to convey at least a portion of the testing gaseous substance to the gas detecting apparatus 116 in order to measure a concentration of a substance in the testing gaseous substance for calibration purposes. In some embodiments, the gaseous substance may be conveyed in a direction due to air flow generated by the pump 107. For example, the pump 107 may generate air flow in the gas flow channel at a location proximate the gas detecting apparatus 116 such as by expelling (i.e., pushing) at least a portion of the testing gaseous substance through a gas outlet disposed adjacent the third valve 105 that is connected to the gas detecting apparatus 116. Thus, at least a portion of the testing gaseous substance may be received through an opening (e.g., the gas outlet) on a surface of the calibration apparatus 102 and flow into the gas detecting apparatus 116.

In some embodiments, the pump 107 may be or comprise, for example, without limitation a compressor, a vacuum pump, a manual pump, a motorized pump or the like. In some examples, the third valve 105 may be configured to actuate (e.g., open) automatically in response to receiving a control signal indicating that the background gaseous substance and liquid substance disposed within the calibration apparatus 102 has been fully transformed (e.g., nebulized, vaporized, dispersed, and/or the like) into the testing gaseous substance. In some examples, the third valve 105 may automatically actuate after a predetermined period of time has elapsed within which it can be assumed that the testing solution is fully nebulized/vaporized within the background gaseous substance (e.g., a time period of 1 minute). In some examples, as the pump 107 generates airflow to expel/push at least a portion of the testing gaseous substance into a gas flow channel of the gas detecting apparatus 116, the air pressure within the housing of the calibration apparatus 102 may decrease. In response to the decreasing air pressure over a period of time, the pressure control element 104 may draw in air through the second valve 103 in order to maintain a constant air pressure within the calibration apparatus 102. In this regard, the pressure control element may, in some examples, comprise a sensing component (e.g., pressure sensor) to monitor the air pressure within at least a portion of the calibration apparatus 102. In various examples, the amount of testing gaseous substance expelled from the calibration apparatus 102 to the gas detecting apparatus can be replaced with air in order to maintain a constant air pressure within the system 100. Unwanted fluctuations in air pressure during calibration of the gas detecting apparatus 116 may also result in inaccurate measurements and therefore lead to device malfunction when the gas detecting apparatus is deployed in the field.

Upon termination of the calibration operations, the testing gaseous substance may be completely purged or expelled via one or more valves of the calibration apparatus 102. For example, the testing gaseous substance may be expelled via the second valve 103, the third valve 105 and/or another dedicated valve.

While FIG. 1 provides an example of a system 100 comprising a calibration apparatus 102 and a gas detecting apparatus 116, it is noted that the scope of the present disclosure is not limited to the example shown in FIG. 1. In some examples, an example system 100 may comprise one or more additional and/or alternative elements, and/or may be structured/positioned differently than those illustrated in FIG. 1.

Figure 2:
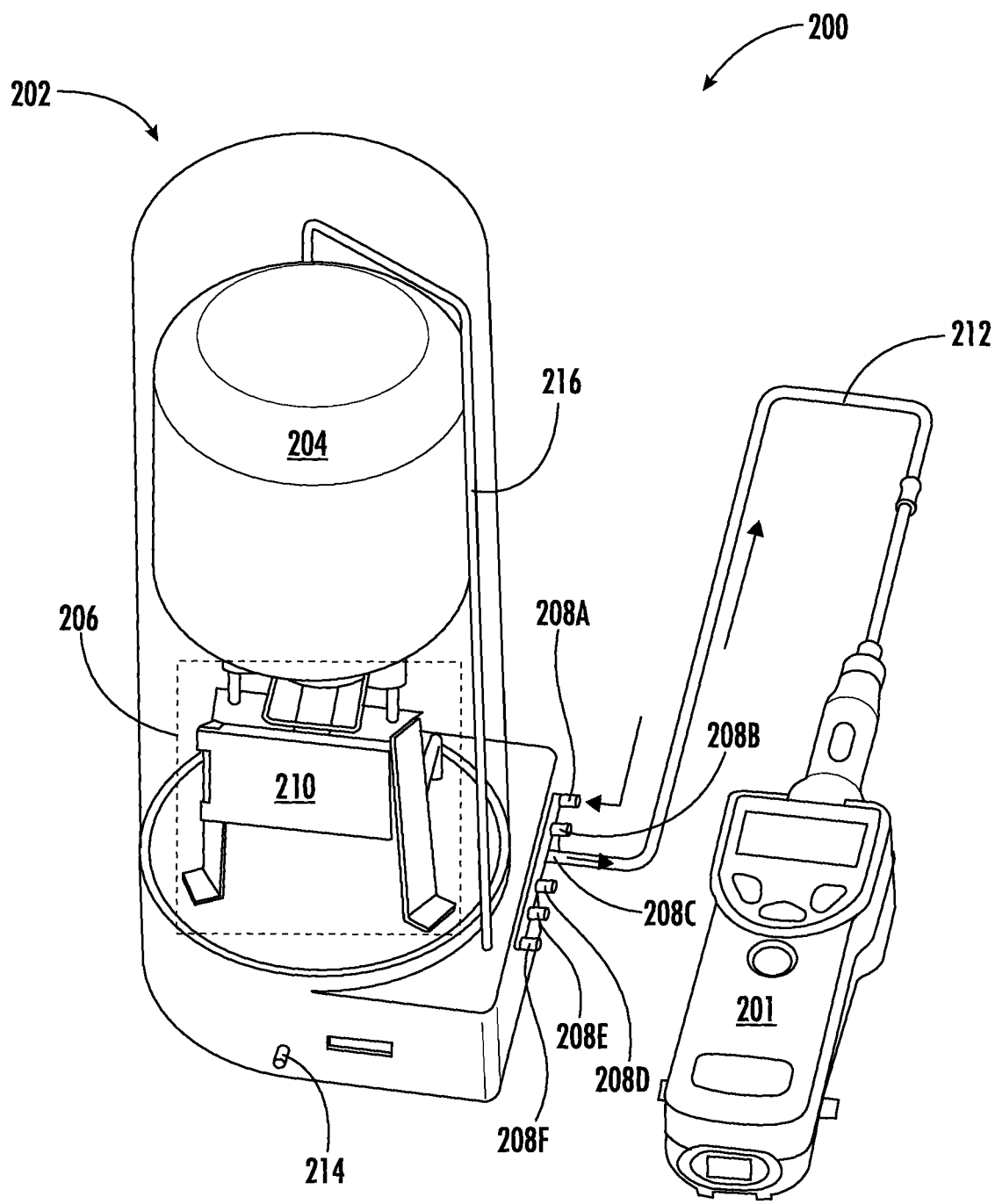
FIG. 2 illustrates an example perspective view depicting a system in accordance with various embodiments of the present disclosure.

Referring now to FIG. 2, an example schematic diagram depicting a perspective view of an example system 200 in accordance with various embodiments of the present disclosure in provided. As depicted, the system 200 comprises a calibration apparatus 202 and a gas detecting apparatus 201. The calibration apparatus 202 may be configured to provide a testing gaseous substance in order to calibrate the gas detecting apparatus 201.

As depicted in FIG. 2, the example system 200 comprises a calibration apparatus 202. As shown, the calibration apparatus 202 comprises a substantially cylindrical housing which may comprise a metallic material (e.g., stainless steel) or plastic material (e.g., Teflon, polycarbonate or the like). The calibration apparatus 202 may be configured to receive a testing solution (e.g., comprising a target compound, a VOC or the like). In some examples, the testing solution may comprise a target compound or VOC dispersed within a liquid solution. The calibration apparatus 202 may be configured to transform the testing solution into a testing gaseous substance in order to calibrate the gas detecting apparatus 201. As depicted in FIG. 2, the calibration apparatus 202 comprises a pressure control element 204, a nebulizing element 206, a first gas inlet/outlet 208A, a second gas inlet/outlet 208B, a third gas inlet/outlet 208C, a fourth gas inlet/outlet 208D, a fifth gas inlet/outlet 208E and a sixth gas inlet/outlet 208F.

The example calibration apparatus 202 may define a gas flow channel 216 which may refer to one or more passageways having at least one gas inlet and at least one gas outlet through which a background gaseous substance and a testing solution may enter, flow through and be expelled from the calibration apparatus 202. The gas flow channel 216 may be or comprise, for example, without limitation, pipes, conduits, tubular structures, and/or the like. As depicted, the gas flow channel 216 defines a conduit connecting the pressure control element 204 to a background gas inlet through which a background gaseous substance may enter the calibration apparatus 202. In some examples, the calibration apparatus 202 may comprise a gas supply element configured to supply the background gaseous substance and, in some examples, a testing solution (e.g., a VOC dispersed in a liquid) to the calibration apparatus 202. The background gaseous substance may flow into the calibration apparatus 202 via the background gas inlet 214 and be conveyed through at least a portion of the gas flow channel 216 until it reaches a portion of the calibration apparatus 202 (e.g., the pressure control element 204 and/or nebulizing element 206).

As noted above, and as depicted in FIG. 2, the calibration apparatus 202 comprises a pressure control element 204. As depicted, the pressure control element 204 is disposed within an upper portion of the housing of the calibration apparatus 202. The pressure control element 204 may be a gas bag or similar device configured to expand and contract based on the amount of a gaseous substance (e.g., air) disposed therein. The example gas bag may comprise textiles, paper or the like. The pressure control element 204 may be configured to regulate/control the air pressure within at least a portion of the calibration apparatus 202. As the background gaseous substance/testing solution flow into the gas flow channel of the calibration apparatus 202, the air pressure within the housing of the calibration apparatus 202 may increase. In response, the pressure control element 204 may then expel displaced air from within the pressure control element 204/calibration apparatus 202 in order to maintain a steady system air pressure within at least a portion of the calibration apparatus 202. Accordingly, a target amount of a background gaseous substance/testing solution having a uniform concentration required for accurate calibration can be provided.

As noted above, and as depicted in FIG. 2, the calibration apparatus 202 comprises a nebulizing element 206. As depicted, the nebulizing element 206 is disposed within a lower portion of the housing of the calibration apparatus 202, beneath/adjacent the pressure control element 204. In various examples, the nebulizing element 206 may be configured such that a testing solution can be deposited directly thereon. For example, the nebulizing element 206 may comprise an aperture, window or the like for receiving the testing solution. As depicted in FIG. 2, the nebulizing element 206 comprises a sealable window 210 through which the testing solution can be deposited (e.g., using a syringe or other similar instrument). In various examples, the nebulizing element 206 operates to transform (e.g., condition, nebulize, aerosolize, vaporize, disperse, and/or the like) the testing solution (e.g., comprising a VOC) in conjunction with the background gaseous substance in order to provide a testing gaseous substance with a uniform concentration of the target substance or compound (e.g., VOC) dispersed therein. In some examples, the nebulizing element 206 may be or comprise an ultrasonic nebulizer. The example ultrasonic nebulizer may operate to transform the testing solution and the background gaseous substance into the testing gaseous substance without heat which may degrade the target substance (e.g., VOC).

As noted above, and as further depicted in FIG. 2, the system 200 comprises a gas detecting apparatus 201 operatively coupled and/or connected to the calibration apparatus 202. In some examples, the gas detecting apparatus 201 may be a PID. The gas detecting apparatus 201 may be connected to the calibration apparatus 202 via a conduit 212 connected to the third gas inlet/outlet 208C of the calibration apparatus 202. In various examples, the gas detecting apparatus 201 may be calibrated when operated in conjunction with the calibration apparatus 202. For instance, during operations, a number of measurements may be taken by the gas detecting apparatus 201 in relation to the testing gaseous substance in order to ensure that the measurements obtained by the gas detecting apparatus 201 satisfy one or more target operational parameters. By way of example, a concentration of a particular VOC dispersed within the testing gaseous substance may be measured by the gas detecting apparatus 201 in order to ensure that the gas detecting apparatus 201 is configured to accurately detect the VOC.

In various examples, the calibration apparatus 202 may be configured to convey at least a portion of the testing gaseous substance to the gas detecting apparatus 201 in order to measure a concentration of a target substance (e.g., VOC) in the testing gaseous substance for calibration purposes. For example, a background gaseous substance and target substance (e.g., Hydrogen Peroxide ($H_2O_2$)) may be provided to the calibration apparatus 202 in order to generate a testing gaseous substance with a target concentration of the target substance, for example, 100 parts-per-million (ppm) of $H_2O_2$. In various examples, the amount of background gaseous substance and target substance required to generate the testing gaseous substance may be determined manually or automatically by a controller component. For example, a controller component may comprise program code instructions for automatically determining an amount of a background gaseous substance and an amount of a testing solution required to produce a target concentration of a testing gaseous substance. An example calculation for producing 100 ppm of $H_2O_2$ is provided in Table 1 below:

TABLE 1

Example calculation for producing 100 ppm of $H_2O_2$

| | Value | Unit |
|---|---|---|
| $H_2O_2$ solution concentration | 30 | grams/Liter (g/L) |
| $H_2O_2$ Relative molecular mass | 34.01 | grams/mol (g/mol) |
| Ideal gas molar volume | 22.4 | Liters/mol (L/mol) |
| Chamber volume | 50 | Liters (L) |
| Target concentration of $H_2O_2$ | 100 | Parts-per-million (ppm) |
| Testing solution volume | 0.000253 | Liters (L) |

As indicated above, 0.000253 L of a testing solution is required to produce a testing gaseous substance with a target concentration of 100 ppm of $H_2O_2$ from a testing solution with a $H_2O_2$ concentration of 30 g/L in a chamber with a volume of 50 L.

Returning to FIG. 2, subsequent to providing a testing gaseous substance by the calibration apparatus 202 (e.g., having a concentration of 100 ppm of the example target substance (e.g., $H_2O_2$)) the gas detecting apparatus 201 can be set to 100 ppm after calibration with the testing gaseous substance.

As noted above, the calibration apparatus 202 comprises a plurality of gas inlet/outlets. As shown, the calibration apparatus 202 comprises a first gas inlet/outlet 208A, a second gas inlet/outlet 208B, a third gas inlet/outlet 208C, a fourth gas inlet/outlet 208D, a fifth gas inlet/outlet 208E and a gas sixth inlet/outlet 208F disposed on a surface of the housing of the calibration apparatus 202. The plurality of gas inlets and/or outlets 208A, 208B, 208C, 208D, 208E and 208F may operate to receive and/or expel gaseous substances (e.g., air, background gaseous substance(s), testing gaseous substance(s) or the like) into and out of the calibration apparatus 202 and between the calibration apparatus 202 and other devices/components (e.g., the gas detecting apparatus 201).

As shown, the calibration apparatus 202 comprises a first gas inlet/outlet 208A which may be a gas inlet/outlet to receive and/or expel gas from the pressure control element 204. As further depicted, the calibration apparatus 202 comprises a third gas outlet 208C which may be a gas inlet/outlet to provide at least a portion of the testing gaseous substance to the gas detecting apparatus 201. In some embodiments, the testing gaseous substance may be conveyed in a direction due to air flow generated by a pump. For example, the pump may generate air flow in the gas flow channel at a location proximate the gas detecting apparatus 201 such as by expelling (i.e., pushing) at least a portion of the testing gaseous substance through the gas inlet/outlet 208C that is connected to the gas detecting apparatus 201. Thus, at least a portion of the testing gaseous substance may be received through the gas inlet/outlet 208C and flow into the gas detecting apparatus 201. The additional gas inlets/outlets 208B, 208D, 208E and 208F may be used to connect the calibration apparatus 202 to other devices and components (e.g., more than one gas detecting apparatus at a time in order to run calibration operation in parallel/simultaneously). Upon termination of the calibration operations, the testing gaseous substance may be completely purged or expelled via the one or more gas inlets/outlets 208A, 208B, 208C, 208D, 208E and 208F of the calibration apparatus 202. For example, the testing gaseous substance may be expelled via the first gas inlet/outlet 208A.

While FIG. 2 provides an example of a system 200 comprising a calibration apparatus 202 and a gas detecting apparatus 201, it is noted that the scope of the present disclosure is not limited to the example shown in FIG. 2. In some examples, an example system 200 may comprise one or more additional and/or alternative elements, and/or may be structured/positioned differently than those illustrated in FIG. 2.

Figure 3:
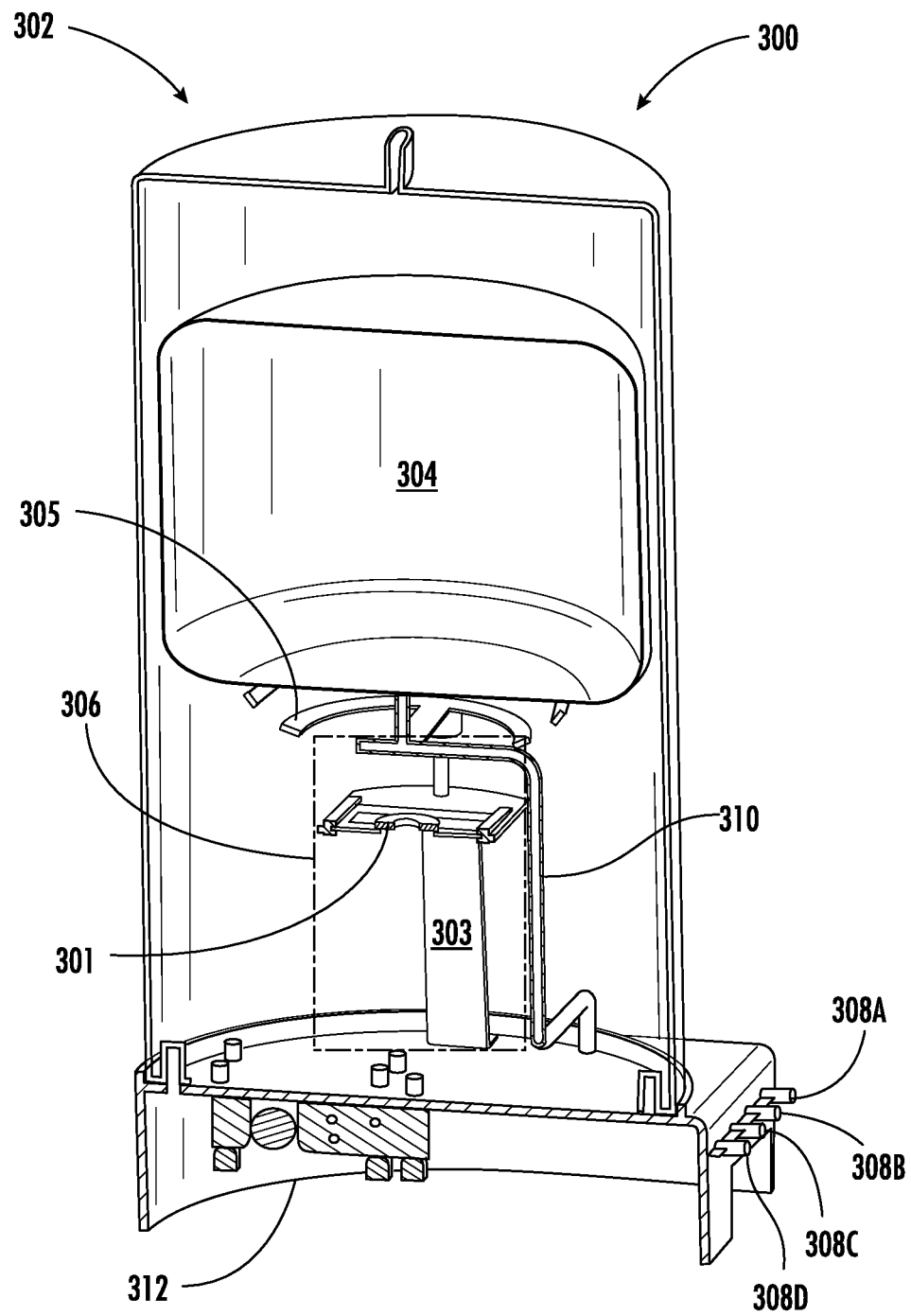
FIG. 3 illustrates a cross section view depicting an apparatus in accordance with various embodiments of the present disclosure.

Referring now to FIG. 3, an example schematic diagram depicting a cross-section view 300 of an example calibration apparatus 302 in accordance with various embodiments of the present disclosure in provided. The calibration apparatus 302 may be configured to provide a testing gaseous substance in order to calibrate a gas detecting apparatus.

As depicted in FIG. 3, the example calibration apparatus 302 comprises a substantially cylindrical housing which may comprise a metal. The calibration apparatus 302 may be configured to receive a testing solution (e.g., a VOC or target compound dispersed in a liquid). The calibration apparatus 302 may be configured to transform the testing solution (e.g., in conjunction with a background gaseous substance) into a testing gaseous substance in order to calibrate the example gas detecting apparatus. As depicted in FIG. 3, the calibration apparatus 302 comprises a pressure control element 304, a nebulizing element 306, a controller component 312, a first gas inlet/outlet 308A, a second gas inlet/outlet 308B, a third gas inlet/outlet 308C and a fourth gas inlet/outlet 308D.

The example calibration apparatus 302 may define a gas flow channel 310 which may refer to one or more passageways having at least one gas inlet and at least one gas outlet through which a background gaseous substance and a testing solution may enter, flow through and be expelled from the calibration apparatus 302. As depicted in FIG. 3, a least a portion of the gas flow channel 310 may connect the pressure control element 304 to the environment (e.g., external air). The gas flow channel 310 may be or comprise, for example, without limitation, pipes, conduits, tubular structures, and/or the like. As depicted, the gas flow channel 310 defines one or more conduits connecting the pressure control element 304 to the nebulizing element 306 and the plurality of gas inlets/outlets 308A, 308B, 308C and 308D. In some examples, the background gaseous substance and testing solution may enter the calibration apparatus 302 through one of the plurality of gas inlets/outlets 308A, 308B, 308C and 308D. In some examples, the calibration apparatus 302 may comprise a gas supply element configured to supply the background gaseous substance and, in some examples, a testing solution (e.g., a VOC dispersed in a liquid) to the calibration apparatus 302. The background gaseous substance may flow into the calibration apparatus 302 via a background gas inlet 214 and be conveyed through at least a portion of the gas flow channel 310 until it reaches a portion of the calibration apparatus 302 (e.g., the pressure control element 304 and/or nebulizing element 306). The plurality of gas inlets/outlets 308A, 308B, 308C and 308D may be used to connect the calibration apparatus 302 to other devices and components (e.g., a gas detecting apparatus). For example, the first gas/inlet 308A may connect the pressure control element 304 to the environment (e.g., external air). Upon termination of the calibration operations, the testing gaseous substance may be completely purged or expelled via one or more of the gas inlets/outlets 308A, 308B, 308C and 308D.

As noted above, and as depicted in FIG. 3, the calibration apparatus 302 comprises a pressure control element 304. As depicted, the pressure control element 304 is disposed within an upper portion of the housing of the calibration apparatus 302. As further depicted in FIG. 3, the pressure control element 304 comprises a support bracket 305 disposed between the pressure control element 304 and the nebulizing element 306 which may provide support for the pressure control element 304. As depicted, the support bracket 305 defines a circular frame and may comprise metal, plastic or any other suitable material. The pressure control element 304 may be a gas bag or similar device configured to expand and contract based on the amount of a gaseous substance (e.g., air) disposed therein. The example gas bag may comprise textiles, paper or the like. The pressure control element 304 may be configured to control the air pressure within at least a portion of the calibration apparatus 302. As the background gaseous substance/testing solution flow through the calibration apparatus 302, the air pressure within the housing of the calibration apparatus 302 may increase. In response, the pressure control element 304 may expel air from within the pressure control element 304/calibration apparatus 302 in order to maintain a steady system air pressure within at least a portion of the calibration apparatus 302. Accordingly, a target amount of a background gaseous substance/testing solution having a uniform concentration required for accurate calibration can be provided.

As noted above, and as depicted in FIG. 3, the calibration apparatus 302 comprises a nebulizing element 306. As depicted, the nebulizing element 306 is disposed within a lower portion of the housing of the calibration apparatus 302, beneath/adjacent the pressure control element 304. Additionally, as depicted, the nebulizing element 306 comprises a nebulizer 301 mounted upon a mounting frame 303. As illustrated, the mounting frame 303 is attached to an inner bottom surface of the calibration apparatus 302 such that the nebulizer 301 is centrally disposed and relatively unconstrained within the calibration apparatus 302. In various examples, the nebulizer 301 may be configured to transform (e.g., condition, nebulize, aerosolize, vaporize, disperse, and/or the like) a testing solution (e.g., comprising a VOC) within the background gaseous substance in order to provide a testing gaseous substance with a uniform concentration of the target substance or compound (e.g., VOC) dispersed therein. In some examples, the nebulizer 301 may be a high-frequency ultrasonic nebulizer. The testing gaseous substance may be provided to a gas detecting apparatus (e.g., a PID) for calibration purposes, for example, via one or more of the plurality of gas inlets/outlets 308A, 308B, 308C and 308D.

In various examples, the calibration apparatus 302 may be configured to convey at least a portion of the testing gaseous substance to the gas detecting apparatus in order to measure a concentration of a target substance (e.g., VOC) in the testing gaseous substance for calibration purposes. As noted above, and as further depicted in FIG. 3, the calibration apparatus 302 comprises a controller component 312. The controller component 312 may be operatively coupled with the calibration apparatus 302 so as to control one or more operating parameters of the calibration apparatus 302. The controller component may exchange (e.g., transmit and receive) data in the form of electrical signals with the calibration apparatus 302 (e.g., with the nebulizing element 306 and the pressure control element 304. For example, the controller component 312 may transmit control signals/control indications to start and stop operations of the nebulizing element 306 and/or the pressure control element 304. By way of example, in response to determining that one or more target parameters of a testing gaseous substance are satisfied (e.g., that the testing solution has been transformed into the testing gaseous substance), the controller component 312 may transmit a control indication to cause actuation of a valve and/or a pump such that at least a portion of the testing gaseous substance enters a gas detecting apparatus operatively connected to the calibration apparatus 302.

While FIG. 3 provides an example of a system comprising a calibration apparatus 302, it is noted that the scope of the present disclosure is not limited to the example shown in FIG. 3. In some examples, an example calibration apparatus 302 may comprise one or more additional and/or alternative elements, and/or may be structured/positioned differently than those illustrated in FIG. 3.

Figure 4:
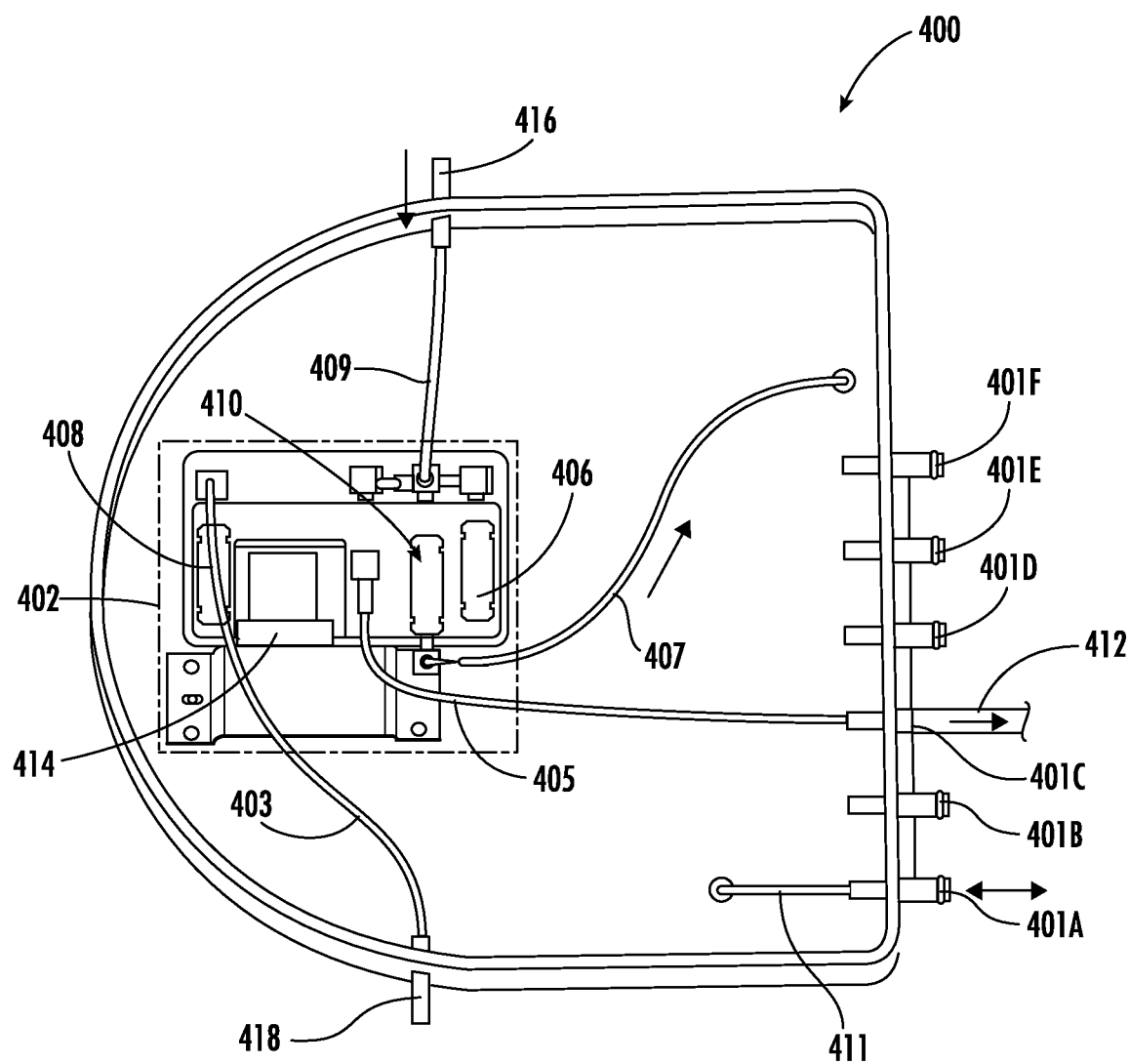
FIG. 4 illustrates a schematic diagram depicting a portion of an apparatus in accordance with various embodiments of the present disclosure.

Referring now to FIG. 4, an example schematic diagram depicting an example portion of a calibration apparatus 400 in accordance with various embodiments of the present disclosure in provided. As depicted, the portion of the calibration apparatus 400 comprises a controller component 402, a first gas inlet/outlet 416, a second gas inlet/outlet 418, a third gas inlet/outlet 401A, a fourth gas inlet/outlet 401B, a fifth gas inlet/outlet 401C, a sixth gas inlet/outlet 401D, 401E and a seventh gas inlet/outlet 401F. The example portion of the calibration apparatus 400 defines a bottom portion/surface of the calibration apparatus 400. The calibration apparatus 400 may be configured to receive a testing solution (e.g., a compound, a VOC or the like dispersed in a liquid). The calibration apparatus 400 may be configured to transform the testing solution (e.g., the VOC or compound dispersed within a liquid solution) into a testing gaseous substance in order to calibrate a gas detecting apparatus.

As depicted in FIG. 4, the example portion of calibration apparatus 400 comprises a controller component 402. As depicted, the controller component 402 may comprise or be operatively connected to a first valve 406, a second valve 408, a third valve 410, and a pump 414. The controller component 402 may operate to control and/or regulate the flow of a gaseous substance within, into and out of the calibration apparatus 400. The example valves 406, 408, 410 may be bi-directional valves configured to permit a gaseous substance to flow in both directions with respect to a location within the gas flow channel.

As depicted in FIG. 4, the example portion of calibration apparatus 400 may define a gas flow channel. The gas flow channel may refer to one or more passageways having at least one gas inlet and at least one gas outlet through which a background gaseous substance and a testing solution may enter, flow through and be expelled from the calibration apparatus 400. The gas flow channel may be or comprise, for example, without limitation, pipes, conduits, tubular structures, and/or the like. As depicted, the gas flow channel of the calibration apparatus 400 comprises a network of tubular structures. As shown, the calibration apparatus comprises a first tubular structure 403, a second tubular structure 405, a third tubular structure 407, a fourth tubular structure 409 and a fifth tubular structure 411 configured to convey a gaseous substance between elements of the calibration apparatus 400 and in and out of the calibration apparatus 400.

As noted above, the calibration apparatus 400 comprises a first gas inlet/outlet 416, a second gas inlet/outlet 418, a third gas inlet/outlet 401A, a fourth gas inlet/outlet 401B, a fifth gas inlet/outlet 401C, a sixth gas inlet/outlet 401D, 401E and a seventh gas inlet/outlet 401F. As depicted, each of the gas inlets/outlets defines an opening on an outer surface of the calibration apparatus 400 and may be connected to the gas flow channel via a tubular structure and valve associated therewith. By way of example, as shown, the first gas inlet/outlet 416 is connected to the third valve 410 and the fourth tubular structure 409. As further depicted, the first valve 406 and the second tubular structure 405 are connected to the fifth gas inlet/outlet 401C. The first valve 406 and the second tubular structure 405 may be configured to convey a background gaseous substance and testing solution (i.e., a testing gaseous solution) into the calibration apparatus 400 (e.g., via a conduit 412 connected to the fifth gas inlet/outlet 401C. In another example, the second gas inlet/outlet 418 is connected to the second valve 408 and the first tubular structure 403. The second gas inlet/outlet 418, the second valve 408 and the first tubular structure 403 may be configured, e.g., in conjunction with output air generated by the pump 414, to expel/purge a gaseous substance from the calibration apparatus 400. As further depicted, the fifth gas inlet/outlet 401C is connected to the second tubular structure 405. The fifth gas inlet/outlet 401C and the second tubular structure 405 (in conjunction with an associated valve 406) may be configured to convey at least a portion of a testing gaseous substance to a gas detecting apparatus via a conduit 412 connected to the fifth gas inlet/outlet 401C. In another example, the third valve 410 and the third tubular structure 407 may be configured to convey at least a portion of a background gaseous substance into the calibration apparatus 400 (e.g., to a nebulizing element of the calibration apparatus 400). In another example, the third gas inlet/outlet 401A may be configured to expel a gaseous substance (e.g., air) from a pressure control element of the controller component 402. In various examples, the controller component 402 may provide (e.g., transmit, send) control signals/control indications to actuate or deactivate the example valves 406, 408 and 410 thereby regulating the flow of gaseous substances within, into and out of the calibration apparatus 400.

While FIG. 4 provides an example portion of a calibration apparatus 400, it is noted that the scope of the present disclosure is not limited to the example shown in FIG. 4. In some examples, an example calibration apparatus 400 may comprise one or more additional and/or alternative elements, and/or may be structured/positioned differently than those illustrated in FIG. 4.

Figure 5:
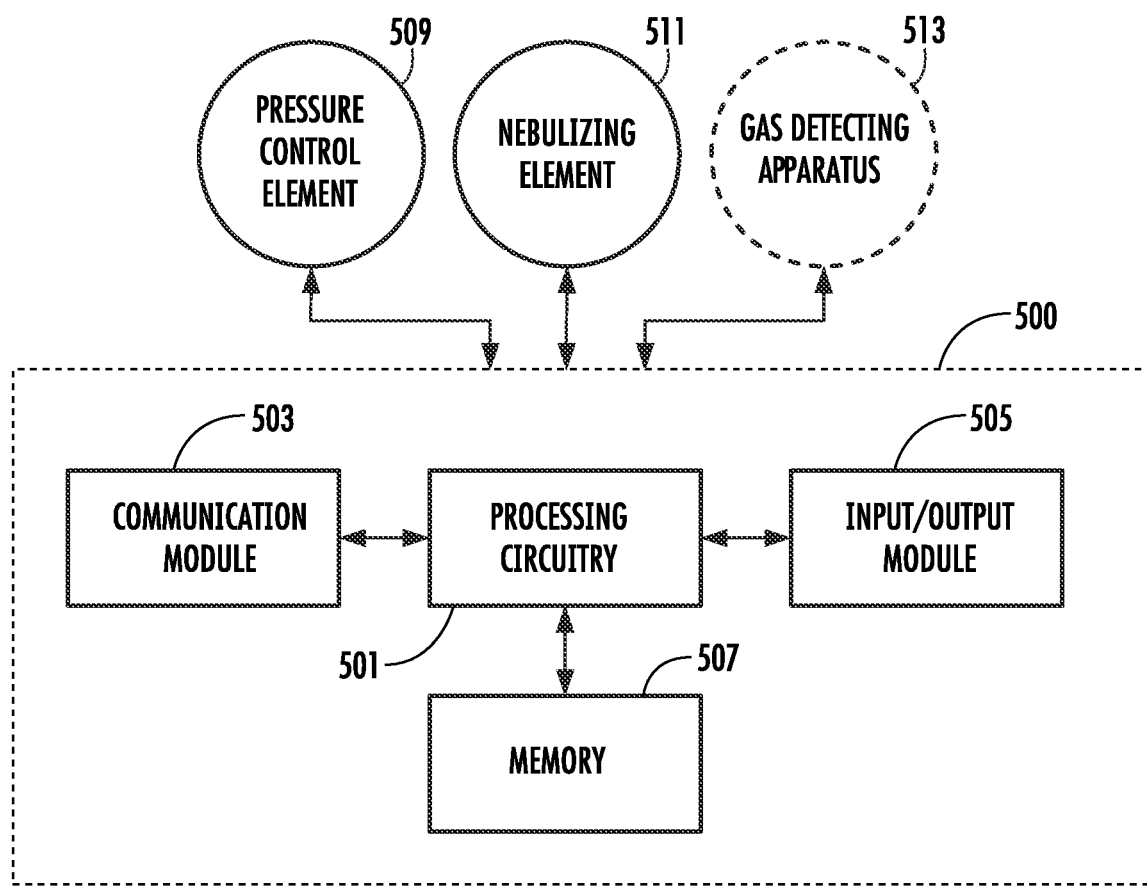
FIG. 5 illustrates an example controller component in electronic communication with various other components of an example apparatus in accordance with various embodiments of the present disclosure.

Referring now to FIG. 5, a schematic diagram depicting an example controller component 500 of an example calibration apparatus in electronic communication with various other components in accordance with various embodiments of the present disclosure is provided. As shown, the controller component 500 comprises processing circuitry 501, a communication module 503, input/output module 505, a memory 507 and/or other components configured to perform various operations, procedures, functions or the like described herein.

As shown, the controller component 500 (such as the processing circuitry 501, communication module 503, input/output module 505 and memory 507) is electrically coupled to and/or in electronic communication with a pressure control element 509, a nebulizing element 511 and, in some examples, a gas detecting apparatus 513. As depicted, each of the pressure control element 509, the nebulizing element 511 and the gas detecting apparatus 513 may exchange (e.g., transmit and receive) data with the processing circuitry 501 of the controller component 500.

The processing circuitry 501 may be implemented as, for example, various devices comprising one or a plurality of microprocessors with accompanying digital signal processors; one or a plurality of processors without accompanying digital signal processors; one or a plurality of coprocessors; one or a plurality of multi-core processors; one or a plurality of controllers; processing circuits; one or a plurality of computers; and various other processing elements (including integrated circuits, such as ASICs or FPGAs, or a certain combination thereof). In some embodiments, the processing circuitry 501 may comprise one or more processors. In one exemplary embodiment, the processing circuitry 501 is configured to execute instructions stored in the memory 507 or otherwise accessible by the processing circuitry 501. When executed by the processing circuitry 501, these instructions may enable the controller component 500 to execute one or a plurality of the functions as described herein. No matter whether it is configured by hardware, firmware/software methods, or a combination thereof, the processing circuitry 501 may comprise entities capable of executing operations according to the embodiments of the present invention when correspondingly configured. Therefore, for example, when the processing circuitry 501 is implemented as an ASIC, an FPGA, or the like, the processing circuitry 501 may comprise specially configured hardware for implementing one or a plurality of operations described herein. Alternatively, as another example, when the processing circuitry 501 is implemented as an actuator of instructions (such as those that may be stored in the memory 507), the instructions may specifically configure the processing circuitry 501 to execute one or a plurality of algorithms and operations described herein, such as those discussed with reference to FIG. 5.

The memory 507 may comprise, for example, a volatile memory, a non-volatile memory, or a certain combination thereof. Although illustrated as a single memory in FIG. 4, the memory 507 may comprise a plurality of memory components. In various embodiments, the memory 507 may comprise, for example, a hard disk drive, a random access memory, a cache memory, a flash memory, a Compact Disc Read-Only Memory (CD-ROM), a Digital Versatile Disk Read-Only Memory (DVD-ROM), an optical disk, a circuit configured to store information, or a certain combination thereof. The memory 507 may be configured to store information, data, application programs, instructions, and etc., so that the controller component 500 can execute various functions according to the embodiments of the present disclosure. For example, in at least some embodiments, the memory 507 is configured to cache input data for processing by the processing circuitry 501. Additionally or alternatively, in at least some embodiments, the memory 507 is configured to store program instructions for execution by the processing circuitry 501. The memory 507 may store information in the form of static and/or dynamic information. When the functions are executed, the stored information may be stored and/or used by the controller component 500.

The communication module 503 may be implemented as any apparatus included in a circuit, hardware, a computer program product or a combination thereof, which is configured to receive and/or transmit data from/to another component or apparatus. The computer program product comprises computer-readable program instructions stored on a computer-readable medium (for example, the memory 507) and executed by a controller component 500 (for example, the processing circuitry 501). In some embodiments, the communication module 503 (as with other components discussed herein) may be at least partially implemented as the processing circuitry 501 or otherwise controlled by the processing circuitry 501. In this regard, the communication module 503 may communicate with the processing circuitry 501, for example, through a bus. The communication module 503 may comprise, for example, antennas, transmitters, receivers, transceivers, network interface cards and/or supporting hardware and/or firmware/software, and is used for establishing communication with another apparatus. The communication module 503 may be configured to receive and/or transmit any data that may be stored by the memory 507 by using any protocol that can be used for communication between apparatuses. The communication module 503 may additionally or alternatively communicate with the memory 507, the input/output module 505 and/or any other component of the controller component 500, for example, through a bus.

In some embodiments, the controller component 500 may comprise an input/output module 505. The input/output module 505 may communicate with the processing circuitry 501 to receive instructions input by the user and/or to provide audible, visual, mechanical or other outputs to the user. Therefore, the input/output module 505 may comprise supporting devices, such as a keyboard, a mouse, a display, a touch screen display, and/or other input/output mechanisms. Alternatively, at least some aspects of the input/output module 505 may be implemented on a device used by the user to communicate with the controller component 500. The input/output module 505 may communicate with the memory 507, the communication module 503 and/or any other component, for example, through a bus. One or a plurality of input/output modules and/or other components may be included in the controller component 500.

For example, the pressure control element 509 may be similar to pressure control element 204 described above with regard to FIG. 2. For example, pressure control element 509 may be configured to regulate/control air pressure within at least a portion of the calibration apparatus. In some embodiments, nebulizing element 511 may be similar to nebulizing element 206 described above with regard to FIG. 2. For example, nebulizing element 511 may be configured to transform a testing solution in conjunction with a background gaseous substance in order to provide a testing gaseous substance. In some embodiments, gas detecting apparatus may be similar to gas detecting apparatus 201 described above with regard to FIG. 2. For example, gas detecting apparatus 413 may generate measurements indicating a concentration level of a testing compound in a testing gaseous substance.

Figure 6:
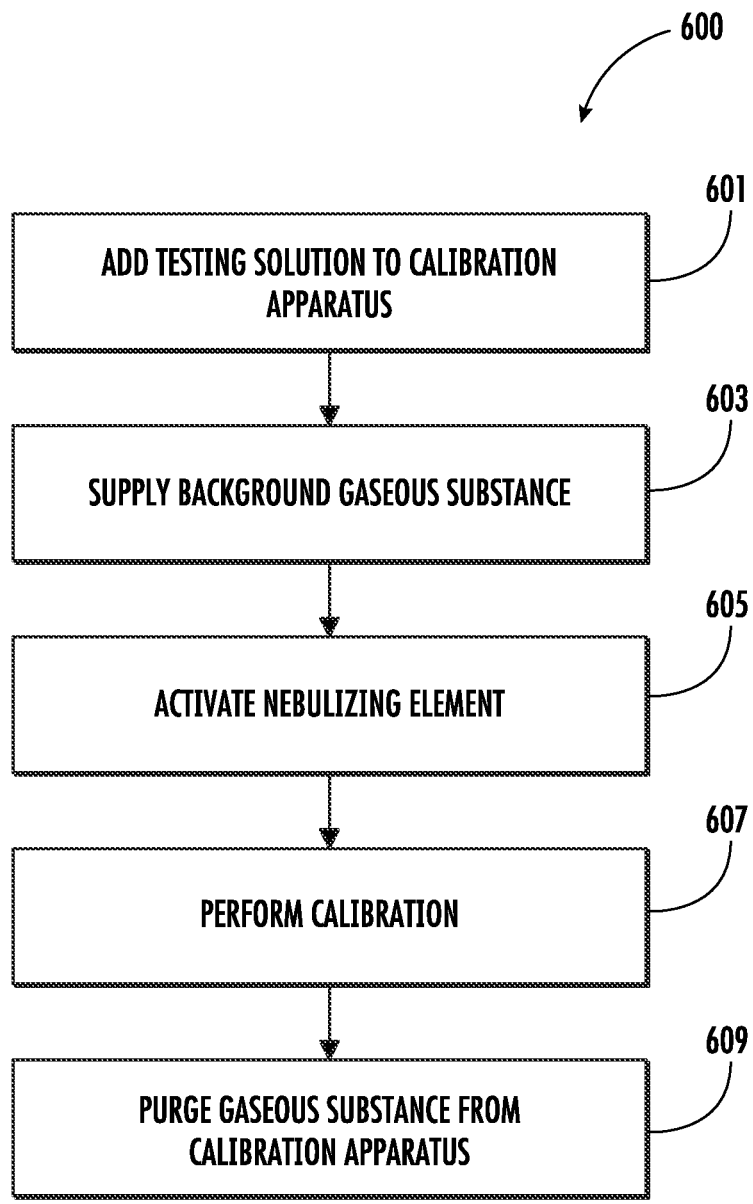
FIG. 6 is a flowchart diagram illustrating example operations in accordance with various embodiments of the present disclosure.

Referring now to FIG. 6, a flowchart diagram illustrating example operations 600 in accordance with various embodiments of the present disclosure is provided.

In some examples, the method 600 may be performed by a processing circuitry (for example, but not limited to, an application-specific integrated circuit (ASIC), a central processing unit (CPU)). In some examples, the processing circuitry may be electrically coupled to and/or in electronic communication with other circuitries of the example apparatus, such as, but not limited to, a pressure control element, a dehumidifier component, a gas detecting, a memory (such as, for example, random access memory (RAM) for storing computer program instructions), and/or a display circuitry (for rendering readings on a display).

In some examples, one or more of the procedures described in FIG. 6 may be embodied by computer program instructions, which may be stored by a memory (such as a non-transitory memory) of a system employing an embodiment of the present disclosure and executed by a processing circuitry (such as a processor) of the system. These computer program instructions may direct the system to function in a particular manner, such that the instructions stored in the memory circuitry produce an article of manufacture, the execution of which implements the function specified in the flow diagram step/operation(s). Further, the system may comprise one or more other circuitries. Various circuitries of the system may be electronically coupled between and/or among each other to transmit and/or receive energy, data and/or information.

In some examples, embodiments may take the form of a computer program product on a non-transitory computer-readable storage medium storing computer-readable program instruction (e.g., computer software). Any suitable computer-readable storage medium may be utilized, including non-transitory hard disks, CD-ROMs, flash memory, optical storage devices, or magnetic storage devices.

The example method 600 begins at step/operation 601. At step/operation 601, a liquid solution is added to the calibration apparatus. The testing solution may be or comprise a testing compound dispersed within a liquid. In some examples, the liquid solution may be deposited into a nebulizing element of the calibration apparatus, such as within a sample window (e.g., sealable window), cavity or the like. In other examples, the liquid solution may be directly deposited into (e.g., mixed with) a background gaseous substance.

Subsequent to step/operation 601, the example method 600 proceeds to step/operation 603. At step/operation 603, a background gaseous substance is supplied to the calibration apparatus. In some examples, the background gaseous substance may be supplied via a gas supply element (e.g., a cylinder). The background gaseous substance and testing solution may enter the calibration apparatus through one or more openings (e.g., gas inlet(s)) on a surface of the housing of the calibration apparatus and be conveyed through the calibration apparatus. By way of example, a testing solution comprising 0.000253 Liters (L) of $H_2O_2$ having a concentration of 30 grams/liter (g/L), a relative molecular mass of 34.01 grams per mole (g/mol) and an ideal gas molar volume of 22.4 L/mol and 50 L of $N_2$ may by provided to produce a testing gaseous substance with a target $H_2O_2$ concentration of 100 ppm. The relative amounts of the liquid solution may be computed manually or determined and/or titrated by the processing circuitry (such as, but not limited to, the processing circuitry 501 of the controller component 500 illustrated in connection with FIG. 5, discussed above). The processing circuitry may provide a control indication to cause the background gaseous substance and/or testing solution to enter the calibration apparatus, such as by actuating one or more valves.

Subsequent to step/operation 603, the method 600 proceeds to step/operation 605. At step/operation 605, the processing circuitry sends a control indication to activate the nebulizing element. The nebulizing element may be configured to transform (e.g., condition, nebulize, vaporize or the like) the testing solution (e.g., in conjunction with the background gaseous substance) into a testing gaseous substance. In the above example of a testing solution comprising $H_2O_2$, the nebulizing element may transform the testing solution into the testing gaseous substance within 10 seconds of the nebulizing element being activated. Additionally, a pressure control element may operate to control the air pressure within at least a portion of the calibration apparatus in order to ensure that a precise amount of a testing gaseous substance is generated by expelling and/or drawing air into the calibration apparatus in response to detecting that the air pressure within the at least a portion of the calibration apparatus is decreasing or increasing, respectively.

Subsequent to step/operation 605, the method 600 proceeds to step/operation 607. At step/operation 607, calibration may be performed, e.g., by providing at least a portion of the testing gaseous substance to a gas detecting apparatus (e.g., a PID). Accordingly, the testing gaseous substance provided by the calibration apparatus may be utilized to calibrate the gas detecting apparatus.

Subsequent to step/operation 607, the method 600 proceeds to step/operation 609. At step/operation 609, after performing calibration operations, the processing circuitry sends a control indication to activate the nebulizing purge or expel the testing gaseous substance via one or more gas inlets/outlets of the calibration apparatus, such as by actuating one or more valves. As described above, the calibration apparatus and the processing circuitry may thus operate to provide a uniform testing gaseous substance for calibration purposes.

Many modifications and other embodiments of the present disclosure set forth herein will come to mind to one skilled in the art to which these embodiments pertain having the benefit of the teachings presented in the foregoing descriptions and the associated drawings. Therefore, it is to be understood that the disclosure are not to be limited to the specific embodiments disclosed and that modifications and other embodiments are intended to be included within the scope of the appended claims. Moreover, although the foregoing descriptions and the associated drawings describe example embodiments in the context of certain example combinations of elements and/or functions, it should be appreciated that different combinations of elements and/or functions may be provided by alternative embodiments without departing from the scope of the appended claims. In this regard, for example, different combinations of elements and/or functions than those explicitly described above are also contemplated as may be set forth in some of the appended claims. Although specific terms are employed herein, they are used in a generic and descriptive sense only and not for purposes of limitation.

The invention claimed is:

1. A calibration apparatus configured to generate a testing gaseous substance, the calibration apparatus comprising:
   a gas supply element configured to provide a background gaseous substance within at least a portion of the calibration apparatus;
   a nebulizing element configured to generate the testing gaseous substance by transforming a testing solution in conjunction with the background gaseous substance;

a pressure control element configured to regulate airflow in order to maintain a constant air pressure within the at least the portion of the calibration apparatus; and a controller component in electronic communication with the gas supply element, the nebulizing element and the pressure control element, wherein the controller component is configured to:

in response to determining that the testing solution is fully transformed, cause the at least the portion of the testing gaseous substance to enter a gas detecting apparatus in conjunction with output of a pump.

2. The calibration apparatus of claim 1, further comprising:

a sealable window disposed adjacent the nebulizing element, wherein the sealable window is configured to receive the testing solution.

3. The calibration apparatus of claim 2, further comprising:

a gas flow channel comprising at least one gas inlet and at least one gas outlet through which a gaseous substance may enter or exit the calibration apparatus.

4. The calibration apparatus of claim 3, further comprising:

at least one valve connected to the gas flow channel configured to regulate a flow of the gaseous substance.

5. The calibration apparatus of claim 4, wherein the at least one valve is disposed between the calibration apparatus and the gas detecting apparatus, and wherein the controller component is further configured to:

in response to determining that the testing gaseous substance satisfies one or more target parameters, transmit a control indication to actuate the at least one valve in order to cause at least the portion of the testing gaseous substance to enter the gas detecting apparatus.

6. The calibration apparatus of claim 5, wherein the gas detecting apparatus comprises a photoionization detector or an infrared leak detector.

7. The calibration apparatus of claim 1, wherein the pressure control element comprises a pressure sensor.

8. The calibration apparatus of claim 1, wherein the pressure control element comprises a gas bag.

9. The calibration apparatus of claim 1, wherein the nebulizing element comprises an ultrasonic nebulizer.

10. A method comprising:

providing, by a gas supply element, a background gaseous substance within at least a portion of a calibration apparatus;

transforming, by a nebulizing element and in conjunction with the background gaseous substance, a testing solution disposed within the at least the portion of the calibration apparatus into a testing gaseous substance;

regulating, by a pressure control element, airflow in order to maintain a constant air pressure within the at least the portion of the calibration apparatus; and in response to determining, by a controller component, that the testing solution is fully transformed, actuating, by the controller component, a pump in order to cause the at least the portion of the testing gaseous substance to enter a gas detecting apparatus in conjunction with output air of the pump.

11. The method of claim 10, further comprising:

depositing, via a sealable window disposed adjacent the nebulizing element, the testing solution.

12. The method of claim 11, wherein the calibration apparatus comprises a gas flow channel comprising at least one gas inlet and at least one gas outlet through which a gaseous substance may enter or exit the calibration apparatus.

13. The method of claim 12, wherein the calibration apparatus comprises at least one valve connected to the gas flow channel configured to regulate a flow of the gaseous substance.

14. The method of claim 13, further comprising:

in response to determining, by the controller component in electronic communication with the nebulizing element and the pressure control element, that the testing gaseous substance satisfies one or more parameters, transmitting, by the controller component, a control indication to actuate the at least one valve.

15. The method of claim 10, wherein the pressure control element comprises a pressure sensor.

16. The method of claim 10, wherein the pressure control element comprises a gas bag.

17. The method of claim 10, wherein the nebulizing element comprises an ultrasonic nebulizer.

18. The method of claim 10, wherein the gas detecting apparatus comprises a photoionization detector or an infrared leak detector.

* * * * *